US012419978B2

(12) United States Patent
Benevenia et al.

(10) Patent No.: US 12,419,978 B2
(45) Date of Patent: *Sep. 23, 2025

(54) ANTIMICROBIAL COMPOSITION FOR INHIBITING MICROBIAL ORGANISMS IN ALLOGRAFT AND THE METHOD THEREOF

(71) Applicant: Rutgers, The State University of New Jersey, New Brunswick, NJ (US)

(72) Inventors: Joseph Benevenia, Montclair, NJ (US); Sheldon S. Lin, Chatham, NJ (US); Michael J. Vives, Newark, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/423,580

(22) Filed: Jan. 26, 2024

(65) Prior Publication Data

US 2024/0157000 A1    May 16, 2024

Related U.S. Application Data

(63) Continuation-in-part of application No. 17/307,493, filed on May 4, 2021, now Pat. No. 12,178,205, and
(Continued)

(51) Int. Cl.
*A61L 2/00* (2006.01)
*A61L 27/36* (2006.01)
(Continued)

(52) U.S. Cl.
CPC ......... *A61L 2/0088* (2013.01); *A61L 27/3608* (2013.01); *A61L 27/3612* (2013.01);
(Continued)

(58) Field of Classification Search
CPC .... A01N 1/0205; A01N 1/0263; A01N 59/16; A61F 2/0095; A61L 2/0088;
(Continued)

(56) References Cited

U.S. PATENT DOCUMENTS

| 4,759,445 A | 7/1988 | McVay |
| 4,813,210 A | 3/1989 | Masuda et al. |

(Continued)

FOREIGN PATENT DOCUMENTS

| JP | 2001-523527 A | 11/2001 |
| JP | 2015113299 A | 6/2015 |
| WO | 08032928 A1 | 3/2008 |

OTHER PUBLICATIONS

Aho, et al: "Clinical Use of Bone Allografts", Annals of Medicine, 1993, 25:4, pp. 403-412, DOI: 10.3109/07853899309147303.
(Continued)

*Primary Examiner* — Jacob K Ackun
(74) *Attorney, Agent, or Firm* — FOX ROTHSCHILD LLP (57) ABSTRACT

Methods for producing allograft tissue by applying an antimicrobial solution to allograft tissue. The antimicrobial solution exhibits antimicrobial activity to make allograft resistant to microbial organisms, such as bacterium. Surface-modified tissue grafts prepared by these methods are also disclosed.

20 Claims, 4 Drawing Sheets

Related U.S. Application Data a continuation-in-part of application No. 15/425,617, filed on Feb. 6, 2017, now Pat. No. 11,224,678.

(60) Provisional application No. 63/019,525, filed on May 4, 2020, provisional application No. 62/293,064, filed on Feb. 9, 2016.

(51) Int. Cl.
*A61L 27/54* (2006.01)
*A61L 101/30* (2006.01)

(52) U.S. Cl.
CPC ............ *A61L 27/54* (2013.01); *A61L 2101/30* (2020.08); *A61L 2300/404* (2013.01)

(58) Field of Classification Search
CPC .. A61L 27/3608; A61L 27/3612; A61L 27/54; A61L 2101/30; A61L 2300/404
USPC .......................................................... 422/28
See application file for complete search history.

(56) References Cited

U.S. PATENT DOCUMENTS

| | | | |
|---|---|---|---|
| 5,454,886 | A | 10/1995 | Burrell et al. |
| 5,520,664 | A | 5/1996 | Bricault, Jr. et al. |
| 5,906,825 | A | 5/1999 | Seabrook, Jr. et al. |
| 6,013,106 | A | 1/2000 | Tweden et al. |
| 6,113,636 | A | 9/2000 | Ogle |
| 6,254,294 | B1 | 7/2001 | Muhar |
| 6,337,052 | B1 | 1/2002 | Rosenwasser |
| 9,238,090 | B1 | 1/2016 | Fette |
| 11,224,678 | B2 * | 1/2022 | Benevenia .......... A61L 27/3687 |
| 12,178,205 | B2 * | 12/2024 | Benevenia ............. A01N 1/124 |
| 2007/0185026 | A1 | 8/2007 | Walsh et al. |
| 2007/0207186 | A1 | 9/2007 | Scanlon et al. |
| 2011/0140316 | A1 | 6/2011 | Bagga et al. |
| 2013/0028981 | A1 | 1/2013 | Gratzer |
| 2013/0277242 | A1 | 10/2013 | Mori |
| 2013/0280223 | A1 | 10/2013 | Owens et al. |
| 2014/0021208 | A1 | 1/2014 | Anti et al. |
| 2014/0147487 | A1 | 5/2014 | Walls |
| 2014/0271779 | A1 | 9/2014 | Bagga et al. |
| 2015/0004249 | A1 | 1/2015 | Lin et al. |
| 2015/0239640 | A1 | 8/2015 | Smith et al. |
| 2015/0351893 | A1 | 12/2015 | Smith et al. |
| 2017/0106119 | A1 | 4/2017 | Skinner et al. |
| 2017/0224871 | A1 | 8/2017 | Benevenia et al. |
| 2019/0274809 | A1 | 9/2019 | Kapec et al. |
| 2019/0358366 | A1 | 11/2019 | Zawko et al. |
| 2020/0207830 | A1 | 7/2020 | Feuerbach et al. |
| 2021/0251215 | A1 | 8/2021 | Benevenia et al. |
| 2021/0308328 | A1 | 10/2021 | Fette |

OTHER PUBLICATIONS

Delloye, et al: "Bone Allografts: What They Can Offer and What They Cannot", 2007, The Bone & Joint Journal, vol. 89, No. 5, pp. 574-579.

Faiz, et al: "Efficacy of Zinc as Antibacterial Agent Against Enteric Bacterial Pathogens", J. Ayub Med Coll Abbottabad, 2011, vol. 23, No. 2, pp. 20.

Lord, et al: "Infection in Bone Allografts", Incidence, Nature, and Treatment, The Journal of Bone and Joint Surgery,. Mar. 1988, vol. 70, pp. 369-376.

Mankin, et al: "Infection in Massive Bone Allografts", Clinical Orthopaedics and Related Research, 2005, No. 432, pp. 210-216.

Maral, et al: "Effectiveness of Human Amnion Preserved Long-Term in Glycerol as a Temporary Biological Dressing", Burns, 1999, 25, pp. 625-635.

Muscolo, et al: "The Use of a Bone Allograft for Reconstruction after Resection of Giant-Cell Tumor Close to the Knee", The Journal of Bone and Joint Surgery, Nov. 1993, vol. 75, No. 11, pp. 1656-1662.

Qayyum et al: Proceedings S.Z.P.G.M.I. vol. 12[1-2], 1998, pp. 8-12.

Tomford, et al: "Frozen Musculoskeletal Allografts, A Study of the Clinical Incidence and Causes of Infection Associated with Their Use", The Journal of Bone and Joint Surgery, Sep. 1990, vol. 72, No. 8, pp. 1137-1143.

\* cited by examiner

ANTIMICROBIAL COMPOSITION FOR INHIBITING MICROBIAL ORGANISMS IN ALLOGRAFT AND THE METHOD THEREOF

CROSS-REFERENCE TO RELATED APPLICATIONS

The present application claims priority benefit under 35 U.S.C. § 120 as a Continuation-In-Part of U.S. patent application Ser. No. 17/307,493 filed May 4, 2021, which claims priority benefit under 35 U.S.C. § 119(e) to U.S. Provisional Patent Application No. 63/019,525 filed May 4, 2020. U.S. patent application Ser. No. 17/307,493 in turn claims priority benefit under 35 U.S.C. § 120 as a Continuation-In-Part of U.S. patent application Ser. No. 15/425,617 filed Feb. 6, 2017, now U.S. Pat. No. 11,224,678, which claims priority benefit under 35 U.S.C. § 119(e) of U.S. Provisional Patent Application No. 62/293,064 filed Feb. 9, 2016. The disclosures of all four applications are incorporated herein by reference in their entirety.

FIELD

The present invention relates in general to a method of preparing a tissue graft to provide improved antimicrobial properties and, in particular, to a method of using a solution of an antimicrobial composition to make allograft resistant to microbial organisms, such as bacterium.

BACKGROUND

Surgeons are frequently faced with reconstruction challenges caused by bone loss. Although autologous bone is the gold standard for bone restoration, donor site morbidity and limited bone volume have led to increased utilization of allograft bone. Approximately 800,000 bone allograft transplantations are performed yearly in the United States, making bone the second most commonly transplanted tissue as described in Boyce et al. Although bone allograft generally restores bone mass, complications such as graft-host non-union, fracture, and graft infection are not infrequent as described in Aho A J (Ann Med. 1993; 25:403-412).

Allograft-associated infection often requires removal of infected bone and extensive debridement of the affected site with substantial patient morbidity. The use of a bone allograft for reconstruction after resection of giant-cell tumor close to the knee (J Bone Joint Surg Am. 1993; 75:1656-1662). Most of these allograft-associated infections can occur early, such as within four months (Lord et al., J Bone Joint Surg Am. 1988; 70:369-376). Despite extended antibiotic prophylaxis, the reported incidence remains at 4% to 12% (Mankin H J et al. Clin Orthop Relat Res. 2005; 432:210-216). Like metallic implants, allografts act as highly porous, non-cellular, and avascular foreign bodies prone to bacterial adhesion.

Approaches have been described for depositing antimicrobial elemental metal and/or metal compounds within a medical article. U.S. Pat. No. 6,113,636 describes chemical, photochemical, and electrochemical processes for depositing elemental metal on and in a biocompatible material such as tissue. Three approaches are described for associating elemental metal with tissue and other biocompatible materials under relatively mild conditions. A first approach involves the reaction of metal solutions with a chemical reductant, such as an unreacted crosslinking agent, which may be present in or added to the tissue. A second approach involves photo-reduction of metal compounds in the presence of a biocompatible material. Finally, elemental metal can be deposited by electrochemical reduction. However, chemical or electrochemical processing can have the shortcomings of being harmful to the tissue and require cumbersome or expensive manufacturing.

Thus, there is a need for methods for processing tissue grafts without chemical or electrochemical processing to obtain tissue grafts resistant to microbial organisms.

SUMMARY

This disclosure addresses the need mentioned above in a number of aspects. In one aspect, this disclosure provides a method for preparing a tissue graft. The method comprises: providing a tissue graft; and applying to the tissue graft an antimicrobial solution comprising a zinc compound by contacting the tissue graft with the antimicrobial solution for about 1 minute to about 24 hours, thereby causing the zinc compound to directly associate with the tissue graft and modify the surface of the allograft tissue, wherein the antimicrobial solution exhibits antimicrobial activity and provides deep tissue cleaning.

In some embodiments, the step of applying comprises contacting the allograft tissue with the antimicrobial solution comprising from about 0.1% to about 0.5% zinc compound by soaking, rinsing, or washing the tissue graft in the antimicrobial solution for about 1 minute to about 7 minutes.

In some embodiments, the step of applying comprises contacting the allograft tissue with the antimicrobial solution comprising from about 0.1% to about 0.5% zinc compound by soaking, rinsing, or washing the tissue graft in the antimicrobial solution for about 7 mins. to about 10 mins.

In some embodiments, the step of applying comprises contacting the allograft tissue with the antimicrobial solution containing from about 0.1% to about 0.5% zinc compound by soaking, rinsing, or washing the tissue graft in the antimicrobial solution for about 10 mins to about 24 hrs.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION

This disclosure relates to a method for preparing a tissue graft (e.g., allograft tissue, autograft tissue, xenograft tissue)

by inhibiting the growth of bacteria in a tissue graft. In one aspect, this disclosure relates to a method for preparing a tissue graft comprising mechanically applying to the tissue graft an antimicrobial solution having an antimicrobial activity to the microbial organism. Preferred antimicrobial solutions include a zinc solution including $Zn^{2+}$ ions. $Zn^{2+}$ ions in the allograft can exhibit antimicrobial properties. The antimicrobial activity of $Zn^{2+}$ depends on its concentration and contact duration.

In some embodiments, the method comprises: providing a tissue graft; and applying to the tissue graft an antimicrobial solution comprising a zinc compound by contacting the tissue graft with the antimicrobial solution for about 1 minute to about 24 hours, thereby causing the zinc compound to directly associate with the tissue graft and modify the surface of the allograft tissue, wherein the antimicrobial solution exhibits antimicrobial activity.

The term "antimicrobial activity" means in the context of the present invention that the antimicrobial of the invention is active in inhibiting, controlling, or combating microbial organisms. In the present application, the conventional definition is applied to the term "microbial organism," which includes bacteria, archaea, protozoa, algae, fungi, viruses, and multicellular animal parasites (helminths). The most common microbes encountered include fungal organisms and/or bacterial organisms, such as gram-positive and gram-negative bacteria. The antimicrobial activity can occur after the allograft is implanted into the body.

In some embodiments, the step of applying comprises applying to the allograft tissue the antimicrobial solution comprising from about 0.1% to about 20% (e.g., 0.1%, 0.2%, 0.3%, 0.4%, 0.5%, 0.7%, 1%, 2%, 3%, 4%, 5%, 6%, 7%, 8%, 9%, 10%, 11%, 12%, 13%, 14%, 15%, 16%, 17%, 18%, 19%, 20%) zinc compound (e.g., zinc chloride) by soaking, rinsing, or washing the tissue graft in the antimicrobial solution for about 1 minute to about 24 hours (e.g., 1 minute, 2 minutes, 3 minutes, 4 minutes, 5 minutes, 6 minutes, 7 minutes, 8 minutes, 9 minutes, 10 minutes, 15 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In some embodiments, the step of applying comprises applying to the allograft tissue the antimicrobial solution comprising from about 0.1% to about 0.5% (e.g., 0.1%, 0.2%, 0.3%, 0.4%, 0.5%) zinc compound (e.g., zinc chloride) by soaking, rinsing, or washing the tissue graft in the antimicrobial solution for about 10 minutes to about 24 hours (e.g., 10 minutes, 15 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In some embodiments, the step of applying comprises applying to the allograft tissue the antimicrobial solution comprising from about 0.1% to about 0.5% (e.g., 0.1%, 0.2%, 0.3%, 0.4%, 0.5%) zinc compound (e.g., zinc chloride) by soaking, rinsing, or washing the tissue graft in the antimicrobial solution for about 1 minute to about 7 minutes (e.g., 1 minute, 2 minutes, 3 minutes, 4 minutes, 5 minutes, 6 minutes, 7 minutes).

In some embodiments, the step of applying comprises applying to the allograft tissue the antimicrobial solution comprising from about 0.1% to about 0.5% (e.g., 0.1%, 0.2%, 0.3%, 0.4%, 0.5%) zinc compound (e.g., zinc chloride) by soaking, rinsing, or washing the tissue graft in the antimicrobial solution for about 7 minutes to about 10 minutes (e.g., 7 minutes, 8 minutes, 9 minutes, 10 minutes).

In some embodiments, the step of applying comprises applying to the allograft tissue the antimicrobial solution comprising from about 5% to about 15% (e.g., 5%, 6%, 7%, 8%, 9%, 10%, 11%, 12%, 13%, 14%, 15%) zinc compound (e.g., zinc chloride) by soaking, rinsing, or washing the tissue graft in the antimicrobial solution for about 1 hour to about 24 hours (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In some embodiments, the step of applying comprises applying to the allograft tissue the antimicrobial solution comprising from about 5% to about 10% (e.g., 5%, 6%, 7%, 8%, 9%, 10%) zinc compound (e.g., zinc chloride) by soaking, rinsing, or washing the tissue graft in the antimicrobial solution for about 1 hour to about 24 hours (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours).

In some embodiments, zinc compounds can be used in the antimicrobial solution in concentrations of about 1 mM to about 100 mM (e.g., 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100 mM). In one embodiment, concentrations of zinc chloride of about 1 mM to about 20 mM (e.g., 1, 2, 3, 4, 5, 6, 7, 8, 9, 10, 11, 12, 13, 14, 15, 16, 17, 18, 19, 20 mM) can be used as the antimicrobial solution.

In some embodiments, the antibacterial activity is the activity for bacterium selected from the tuberculosis complex microorganisms (e.g., *Mycobacterium tuberculosis.*, *Mycobacterium bovis*, *Mycobacterium africanum*), *Pseudomonas aeruginosa*, *Staphylococcus aureus*, *Aspergillus brasiliensis* spores, and *Escherichia coli*.

In some embodiments, contacting the tissue graft with the antimicrobial solution comprises soaking, rinsing, or washing the tissue graft in the antimicrobial solution.

Examples of zinc compounds suitable for use in the antimicrobial solution may include inorganic zinc compounds, such as mineral acid zinc salts. Examples of inorganic zinc compounds include, but are not limited to, zinc chloride, zinc sulfate, zinc phosphate, zinc carbonate, and zinc nitrate, zinc chlorate, zinc chromate, or combinations thereof.

Examples of zinc compounds suitable for use in the antimicrobial solution can also be zinc salts of organic acids. Examples of organic acid zinc salts include, but are not limited to, Zn acetate, Zn formate, Zn propionate, Zn gluconate, bis(maltolato)Zn, Zn acexamate, Zn aspartate, bis(maltolato)Zn(II) [Zn(ma)2], bis(2-hydroxypyridine-N-oxido)Zn(II) [Zn(hpo)2], bis(allixinato)Zn(II) [Zn(alx)2], bis(6-methylpicolinato)Zn(II), [Zn(6mpa)2], bis(aspirinato)Zn(II), bis(pyrrole-2-carboxylato)Zn [Zn(pc)2], bis(alpha-furonic-acidato)Zn [Zn(fa)2], bis(thiophene-2-carboxylato)Zn [Zn(tc)2], bis(thiophene-2-acetato)Zn [Zn(ta)2], (N-acetyl-L-cysteinato)Zn(II) [Zn(nac)], Zn(II)/poly(γ-glutamic acid) [Zn(γ-pga)], bis(pyrrolidine-N-dithiocarbamate) Zn(II) [Zn(pdc)2], Zn(II) L-lactate [Zn(lac)2], Zn(II) D-(2)-quinic acid [Zn(qui)2], bis(1,6-dimethyl-3-hydroxy-5-methoxy-2-pentyl-1,4-dihydropyridine-4-thion-ato)Zn(II) [Zn(tanm)2], β-alanyl-L-histidinato Zn(II) (AHZ), or the like, or combinations thereof. In another embodiment, the organic acid of zinc salt is a naturally occurring fatty acid.

In some embodiments, the antimicrobial solution comprises Zn 2+ ions.

In some embodiments, the tissue graft comprises a tissue selected from allograft bone, autograft bone, xenograft bone, allograft cartilage, amniotic tissue, ligament tissue, tendon tissue, porous tissue, soft tissue, and a combination thereof. In some embodiments, the tissue graft comprises an allograft tissue. In some embodiments, the allograft tissue comprises allograft bone. In some embodiments, the tissue graft comprises amniotic tissue. In some embodiments, the tissue graft comprises allograft cartilage.

Alternatively, allograft bone was rinsed with the antimicrobial solution such as by the Shake Flask Method (ASTM E2149). For example, the allograft bone can be rinsed in the antimicrobial solution for from about 45 minutes to about 120 minutes.

In some embodiments, the antimicrobial solution further comprises a pharmaceutically acceptable vehicle, excipient, diluent, or adjuvant.

For purposes of the following description, allograft bone is referred to as an exemplary tissue that may be processed according to the present method. However, those skilled in the art will recognize that other tissues, including but not limited to autograft bone, xenograft bone, allograft cartilage, allograft amniotic tissue, other porous tissues, synthetic porous materials, and various soft tissues, may be processed according to the principles defined herein, without departing from the spirit of the invention exemplified herein by reference to allograft bone material. Suitable allograft cartilage can be allograft cartilage manufactured by ANTHREX as BioCartilage®. In one embodiment, ligament or a tendon.

In some embodiments, the patient is a mammalian animal, e.g., a human.

In some embodiments, the method as disclosed herein can be used in combination with an allograft method, autograft method, xenograft method, alloplastic graft method, or orthopedic biocomposite method.

In another aspect, this disclosure also provides a tissue graft prepared by a method as disclosed herein. In some embodiments, the tissue graft is penetrated by the antimicrobial solution and comprises a surface of the tissue graft modified by the zinc compound. In some embodiments, the tissue graft comprises a tissue selected from allograft bone, autograft bone, xenograft bone, allograft cartilage, amniotic tissue, ligament tissue, tendon tissue, porous tissue, soft tissue, and a combination thereof. In some embodiments, the tissue graft comprises an allograft tissue. In some embodiments, the allograft tissue comprises allograft bone. In some embodiments, the tissue graft comprises amniotic tissue. In some embodiments, the tissue graft comprises allograft cartilage.

In yet another aspect, this disclosure provides a kit comprising a tissue graft as disclosed herein. In some embodiments, the kit also includes one or more additional agents (e.g., an antimicrobial solution) contained in the same or different container from the tissue graft. For example, the kit may include a tissue graft provided in a separate container or a separate compartment from the additional agents. In some embodiments, the kit may include informational material. The informational material can be descriptive, instructional, marketing or other material that relates to the tissue graft as prepared by the disclosed methods.

As used herein, a "subject," "subject," or "individual" refers to a human and a non-human animal. Examples of a non-human animal include all vertebrates, e.g., mammals, such as non-human mammals, non-human primates (particularly higher primates), dog, rodent (e.g., mouse or rat), guinea pig, cat, and rabbit, and non-mammals, such as birds, amphibians, reptiles, etc. In one embodiment, the subject is a human. In another embodiment, the subject is an experimental animal or animal suitable as a disease model.

As used herein, the term "pharmaceutically acceptable" refers to a material, such as a carrier or diluent, which does not abrogate the biological activity or properties of the antimicrobial solution, and is relatively non-toxic, i.e., the material may be administered to an individual without causing undesirable biological effects or interacting in a deleterious manner with any of the components of the composition in which it is contained.

As used herein, the term "contacting," when used in reference to any set of components, includes any process whereby the components to be contacted are mixed into the same mixture (for example, are added into the same compartment or solution), and does not necessarily require actual physical contact between the recited components. The recited components can be contacted in any order or any combination (or sub-combination) and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism such as a non-human animal.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the present disclosure.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of this disclosure unless otherwise claimed. No language in the specification should be construed as indicating any non-claimed element as essential to the practice of the invention. When used in this document, the term "exemplary" is intended to mean "by way of example" and is not intended to indicate that a particular exemplary item is preferred or required.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present disclosure. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The present application is a continuation-in-part of U.S. Nonprovisional patent application Ser. No. 17/307,493 ("the '493 application") on systems and methods for storing and preserving an implantable device. The present application is related to U.S. Pat. No. 11,224,678 ("the '678 patent") on a method for producing allograft tissue by applying an antimicrobial solution to allograft tissue. Subsequent to the Examples performed in the '493 application and the '678 patent, which are incorporated herein by reference, the Examples in the present application were performed to investigate the rapidity of zinc binding in human allograft tissue and the rapidity of the antimicrobial effect.

Example 1

Materials and Methods

Figure 1:
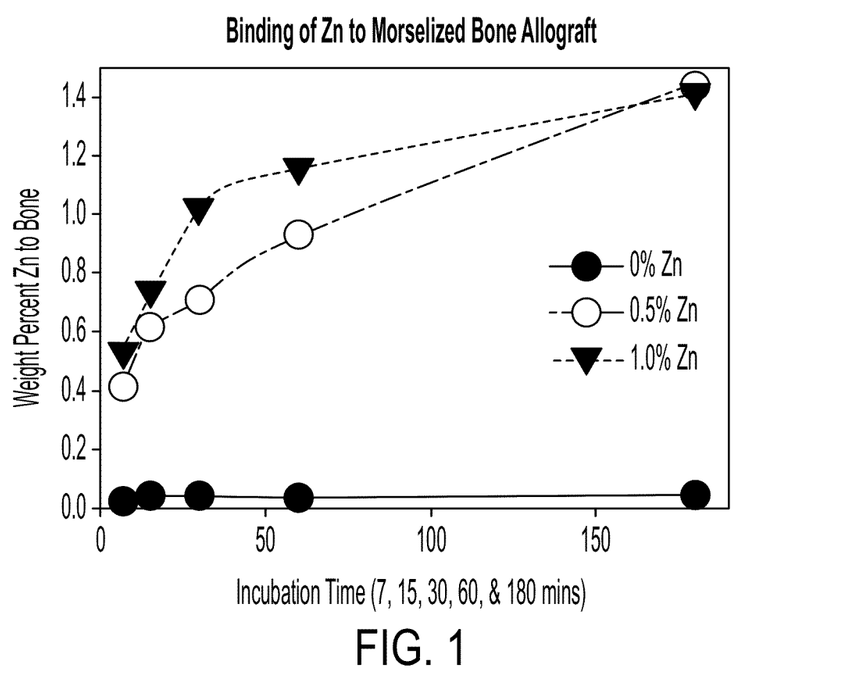
FIG. 1 depicts the quantity of zinc binding to morselized bone allograft over time.

Allograft bone chips (Frontier Spine) were incubated in Tris-buffered saline (TBS) containing different concentrations of zinc chloride (0, 0.5% and 1.0% wt/vol) to evaluate the effect of zinc concentration on zinc adsorption. To measure time dependent adsorption of zinc to cancellous bone chips, 0.2 g samples of bone chips were incubated in 10 mL of either 0%, 0.5% or 1% zinc chloride in TBS for 7 minutes, 15 minutes, 30 minutes, 60 minutes, and 180 minutes. Control bone chips were incubated in TBS alone. After incubation, the bone chips were centrifuged at 500 rpm for 2 minutes and the TBS and Zn-TBS solutions were carefully aspirated out. Bone chips from all the groups were washed in TBS, centrifuged and the buffer was aspirated. After 5 washes, 0.2 g of treated and control bone chips were digested in 3 mL of 60% concentrated nitric acid in a water bath at 40° C. for 4 hours. A 50 µl aliquot of the resulting extract was then diluted 100 times into 4.95 mL of distilled water. Sample zinc levels were analyzed using inductively coupled plasma mass spectrometry. (ICPMS; Agilent ICP-MS 7900, Agilent technologies, Santa Clara). FIG. 1 depicts the quantity of zinc binding to morselized bone allograft after various incubation periods.

TABLE 1

Zn Levels in Human Allograft after $ZnCl_2$ Antimicrobial Wash Post Processed Human Allograft

| $ZnCl_2$ % | Time (mins) | Zn % w/w |
|---|---|---|
| 0 | 7 | 0.022471 |
| 0.5 | 7 | 0.411457 |
| 1 | 7 | 0.533489 |
| 0 | 15 | 0.040175 |
| 0.5 | 15 | 0.616374 |
| 1 | 15 | 0.739788 |
| 0 | 30 | 0.040704 |
| 0.5 | 30 | 0.70731 |
| 1 | 30 | 1.024634 |
| 0 | 60 | 0.036176 |
| 0.5 | 60 | 0.929525 |
| 1 | 60 | 1.159283 |
| 0 | 180 | 0.043805 |
| 0.5 | 180 | 1.443266 |
| 1 | 180 | 1.411757 |

| Time (mins) | 0% $ZnCl_2$ | 0.5% $ZnCl_2$ | 1.0% $ZnCl_2$ |
|---|---|---|---|
| 7 | 0.022471 | 0.411457 | 0.533489 |
| 15 | 0.040175 | 0.616374 | 0.739788 |
| 30 | 0.040704 | 0.70731 | 1.024634 |
| 60 | 0.036176 | 0.929525 | 1.159283 |
| 180 | 0.043805 | 1.443266 | 1.411757 |

Example 2

Materials and Methods

Figure 2:
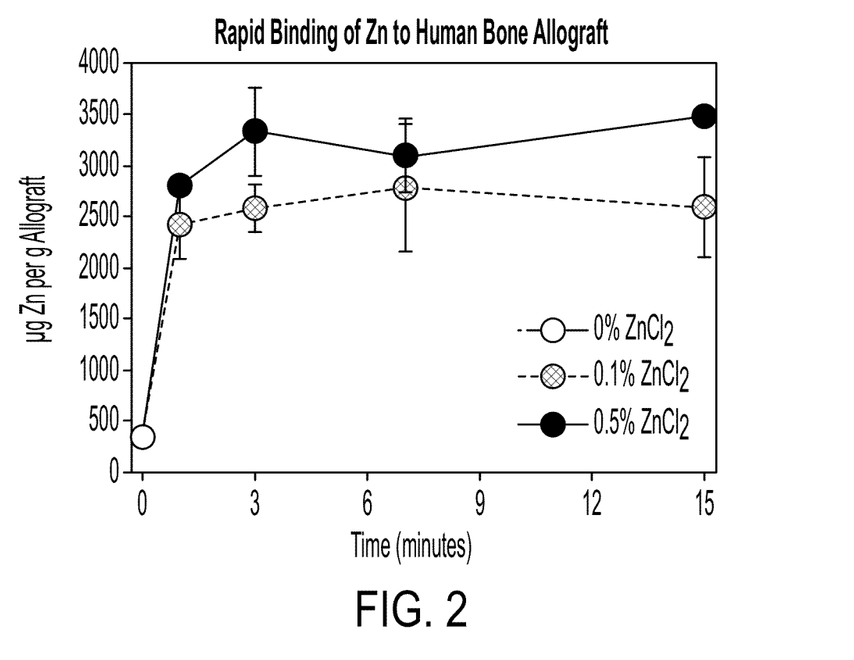
FIG. 2 depicts the quantity of zinc binding to human bone allograft over time.
Figure 3A:
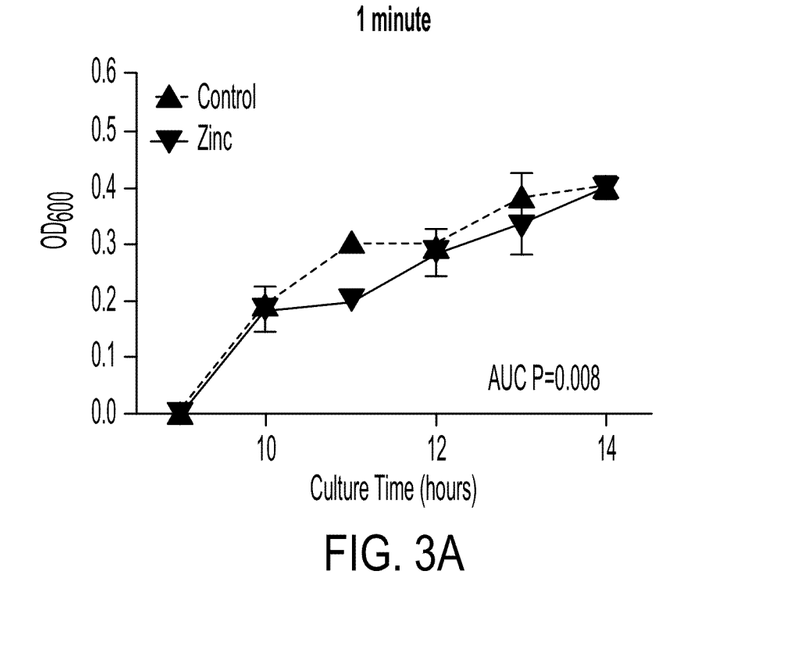
FIGS. 3A, 3B, 3C, 3D and 3E depict the mean $OD_{600}$ values for TBS and Zn-treated wash time trials.
Figure 3B:
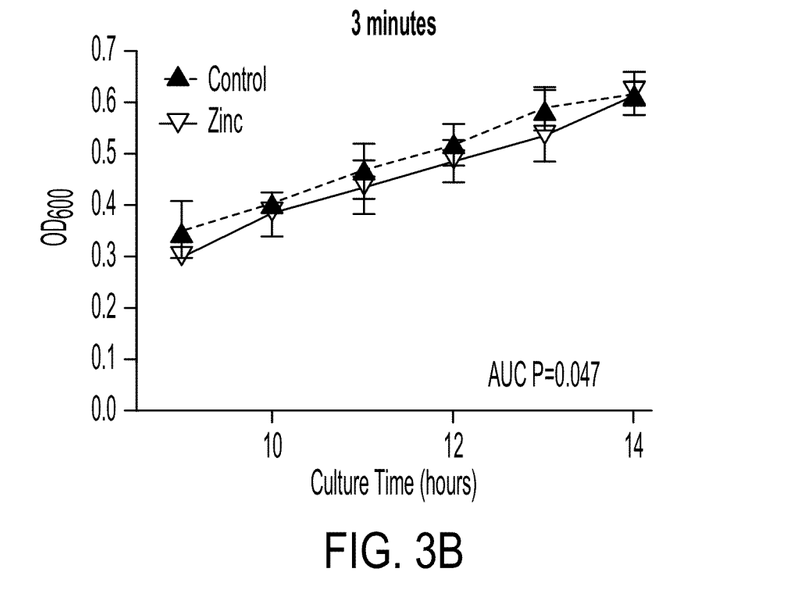
Figure 3C:
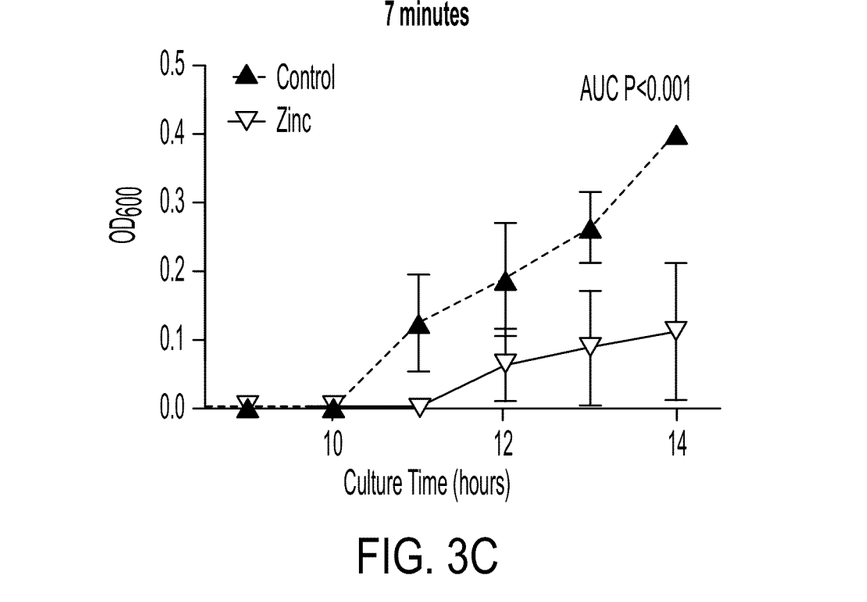
Figure 3D:
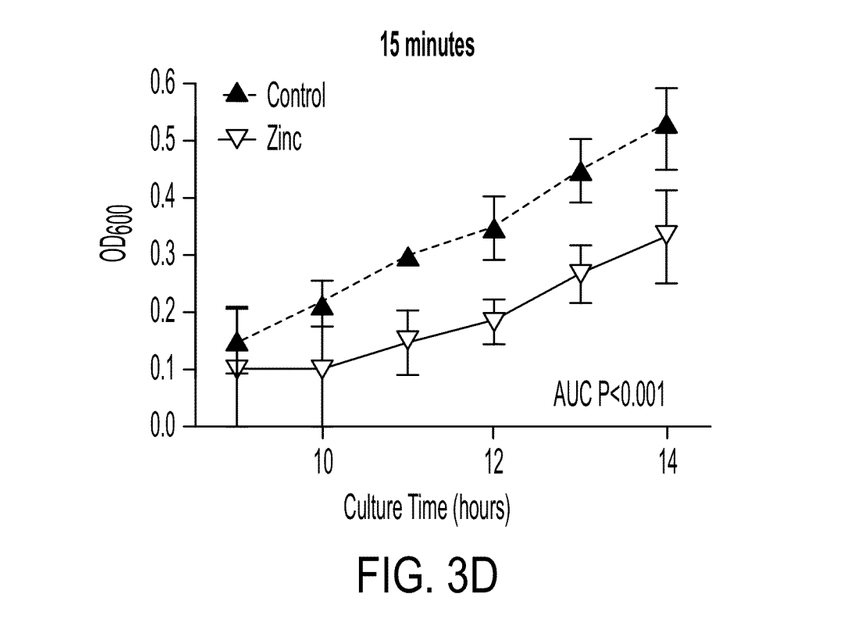
Figure 3E:
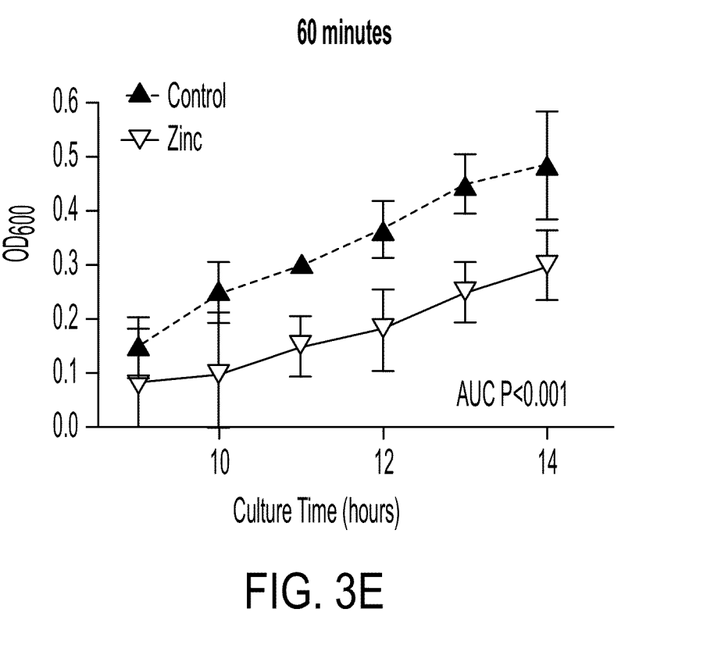

Allograft bone chips were incubated in Tris-buffered saline (TBS) containing different concentrations of zinc chloride (0, 0.5% and 1.0% wt/vol) to evaluate the effect of zinc concentration on zinc adsorption. To measure time dependent adsorption of zinc to cancellous bone chips, 0.2 g samples of bone chips were incubated in 10 mL of either 0%, 0.5% or 1% zinc chloride in TBS for 1, 3, 7, and 15 minutes. Control bone chips were incubated in TBS alone. After incubation, the bone chips were centrifuged at 500 rpm for 2 mins and the TBS and Zn-TBS solutions were carefully aspirated out. Bone chips from all the groups were washed in TBS, centrifuged and the buffer was aspirated. After 5 washes, 0.2 g of treated and control bone chips were digested in 3 mL of 60% concentrated nitric acid in a water bath at 40° C. for 4 hours. A 50 µl aliquot of the resulting extract was then diluted 100 times into 4.95 mL of distilled water. Sample zinc levels were analyzed using inductively coupled plasma mass spectrometry (ICPMS; Agilent ICP-MS 7900, Agilent technologies, Santa Clara). FIG. 2 depicts the quantity of zinc binding to human bone allograft after various incubation periods.

TABLE 2

Zinc Binding to Morselized Human Bone Allograft -
Short-term Zinc Biding to Allograft

| Binding Time | 0% $ZnCl_2$ | 0.1% $ZnCl_2$ | 0.5% $ZnCl_2$ |
|---|---|---|---|
| | Weight Percent Zinc Bound (mean ± SD) | | |
| 1 min | — | 0.242 ± 0.034 | 0.281 ± 0.004 |
| 3 min | — | 0.259 ± 0.023 | 0.334 ± 0.043 |
| 7 min | — | 0.279 ± 0.062 | 0.310 ± 0.036 |
| 15 min | 0.034 + 0.002 | 0.260 ± 0.049 | 0.349 ± 0.007 |

Group Size: 3 per time point per Zn concentration
Results: Level of zinc loading of post processed human allograft achieved at 1, 3, 7 and 15 minutes $ZnCl_2$ antimicrobial wash was between 0.25-0.35% weight by weight.

TABLE 3

Zinc Binding to Morselized Human Bone Allograft -
2-Way ANOVA Statistical Analysis (P < 0.001)
Comparisons Between Zn Conc. (Holm-Sidak Method, p values)

| | 0% $ZnCl_2$ | 0.1% $ZnCl_2$ | 0.5% $ZnCl_2$ |
|---|---|---|---|
| 0% $ZnCl_2$ | — | | |
| 0.1% $ZnCl_2$ | <0.001 | — | |
| 0.5% $ZnCl_2$ | <0.001 | <0.001 | — |

P value for binding time: not significant.

Example 3

Materials and Methods

1. Preparation of *Staphylococcus aureus*

*Staphylococcus aureus* (Staph-A) strain NCTC 8532 [IAM 12544, R. Hugh 2605] was purchased from ATCC as a frozen stock. An aliquot of the frozen stock was initially cultured in Difco Nutrient Broth agar plates overnight at 37° C. Colonies of Staph-A from the plates were used to inoculate 3 mL cultures of Difco Nutrient Broth that were grown overnight at 37° C. with shaking. The overnight cultures were diluted to an optical density ($OD_{600}$) value of 0.1 (equal to $10^7$ CFU/mL) into fresh Difco Nutrient Broth in preparation for treating the bone allograft. Only fresh, overnight cultures were used for experiments.

2. Allograft Source, Preparation, and Treatment with Zinc Chloride ($ZnCl_2$)

Unless otherwise indicated, all procedures were performed at room temperature. Human cancellous bone chips were ground with a sterilized mortar and pestle and then sized using sieves. Allograft aliquots (0.15 g) were placed in 15 mL conical centrifuge tubes. The allograft aliquots were divided into two groups: zinc-treated (Zn-treated) and controls (TBS-treated). For the Zn-treated groups, allograft aliquots were washed with 3 mL of 0.5% $ZnCl_2$ solution and for the TBS-treated, allograft aliquots were washed with 3 mL of Tris-buffered saline (TBS; pH 7.4). The allograft aliquots were sub-divided into 5 subgroups based on washing times of 1, 3, 7, 15, or 60 minutes for both the $ZnCl_2$ solution and the control TBS solution. After the initial Zn or TBS wash, all samples were washed 6 times with 3 mL of TBS for 3 minutes each. The allograft chips were separated from the wash solution using spin-filter cartridges (500 RPM, 180 seconds, Eppendorf 5810R). The allograft bone chips were then sterilized by gamma-irradiation (18 Gy) and stored at room temperature.

3. Allograft Treatment with Staph-A, Post-Treatment Washing and Incubation in Difco Nutrient Broth Fresh, overnight cultures of Staph-A were diluted to $10^3$ CFU/mL in TBS solution (pH 7.4). The Zn-treated and TBS-treated allograft aliquots were exposed to Staph-A by adding 3 mL of $10^3$ CFU/mL to each 0.15 g aliquot of allograft and incubating at 37° C., with shaking, for 30 minutes. Following Staph-A exposure, allograft aliquots were washed 6 times with TBS as described above. After washing, 10 mL of Difco Nutrient Broth was added to each aliquot and cultured at 37° C. with shaking for 14 hours.

4. Data Collection and Analysis

Bacterial growth was monitored by removing 1 mL of culture media and measuring $OD_{600}$ after 9, 10, 11, 12, 13, and 14 hours using an Eppendorf 5810R. A minimum of 6 TBS-treated and Zn-treated allograft aliquots were assayed for Staph-A growth for each wash time (1, 3, 7, 15 and 60 mins). The $OD_{600}$ values were plotted vs. culture time (9-14 hours) for each allograft aliquot and the area under the curve calculated (SigmaPlot v15). The AUCs for the TBS-treated and $ZnCl_2$-treated allograft aliquots at each wash time were compared using unpaired t-tests with Welch's correction. All TBS-treated aliquot AUCs were compared to the AUCs for Zn-treated wash time using ANOVA and post-hoc Tukey tests. Mean $OD_{600}$ values at each time point and for each wash time were also plotted for each TBS-treated and Zn-treated wash time.

5. Media and Other Solutions

The Difco Nutrient Agar formula is per liter: 3 g of beef extract, 5 g of peptone, and 15 g of agar. Agar medium was made by dissolving 18.4 g of Difco Nutrient Agar into 800 mL of water in an Erlenmeyer flask. The solution was then autoclaved at 121° C. for 40 minutes. Difco Nutrient Broth formular is per liter: 3 g of beef extract and 5 g of peptone. Difco Nutrient Broth was made by dissolving 6.4 g in 800 mL of water in an Erlenmeyer flask. The broth was sterilized by autoclaving at 121° C. for 40 minutes. Tris-buffered saline (TBS; pH 7.4) solution utilized in the experiment was made from a 10×TBS stock solution (per liter: 350.8 g NaCl, 96.0 g Trizma base SIGMA T6066; pH 7.69) and water. The 0.5% $ZnCl_2$ solution was prepared with water (0.5 g of $ZnCl_2$ in 100 mL of water).

The FIG. 3 drawings show the mean $OD_{600}$ values for TBS and Zn-treated wash time trials. $OD_{600}$ data were collected at 9, 10, 11, 12, 13, and 14 hours after the addition of nutrient broth to the washed allograft chips. In particular, FIGS. 3A, 3B, 3C, 3D and 3E show the $OD_{600}$ values after 0.5% $ZnCl_2$ or TBS initial wash times of 1, 3, 7, 15, and 60 mins, respectively. The TBS and Zn-treated data from within each wash time were compared by unpaired t-tests. P values are shown, and are statistically significant.

It is understood that the above-described embodiments are illustrative of only a few of the many possible specific embodiments that can represent applications of the principles of the invention. Numerous and varied other arrangements can be readily devised in accordance with these principles by those skilled in the art without departing from the spirit and scope of the invention.

What is claimed is:

1. A method for producing allograft tissue comprising the step of:
providing a tissue graft; and
applying to the tissue graft an antimicrobial solution comprising a zinc compound by contacting the tissue graft with the antimicrobial solution for about 1 minute to about 24 hours.

2. The method of claim 1, wherein the step of applying comprises contacting the allograft tissue with the antimicrobial solution comprising from about 0.1% to about 0.5% zinc compound by soaking, rinsing, or washing the tissue graft in the antimicrobial solution for about 10 minutes to about 24 hours.

3. The method of claim 1, wherein the step of applying comprises applying to the allograft tissue the antimicrobial solution comprising from about 0.1% to about 0.5% zinc compound by soaking, rinsing, or washing the tissue graft in the antimicrobial solution for about 1 minute to about 2 hours.

4. The method of claim 1, wherein the step of applying comprises applying to the allograft tissue the antimicrobial solution comprising from about 0.1% to about 0.5% zinc compound by soaking, rinsing, or washing the tissue graft in the antimicrobial solution for about 1 minute to about 7 minutes.

5. The method of claim 1, wherein the step of applying comprises applying to the allograft tissue the antimicrobial solution comprising from about 0.1% to about 0.5% zinc compound by soaking, rinsing, or washing the tissue graft in the antimicrobial solution for about 7 minutes to about 10 minutes.

6. The method of claim 1, wherein the zinc compound is selected from the group consisting of zinc chloride, zinc sulfate, zinc phosphate, zinc carbonate, and zinc nitrate, zinc chlorate, zinc chromate, and combinations thereof.

7. The method of claim 1, wherein the zinc compound is zinc chloride.

8. The method of claim 1, wherein the zinc compound is a zinc salt selected from the group consisting of Zn acetate, Zn formate, Zn propionate, Zn gluconate, bis(maltolato)Zn, Zn acexamate, Zn aspartate, bis(maltolato)Zn(II) [Zn(ma)2], bis(2-hydroxy-pyridine-N-oxido)Zn(II) [Zn(hpo)2], bis(allixinato)Zn(II) [Zn(alx)2], bis(6-methylpicolinato)Zn(II) [Zn(6mpa)2], bis(aspirinato)Zn(II), bis(pyrrole-2-carboxylato) zinc [Zn(pc)2], bis(alpha-furonic acidato)zinc [Zn(fa)2], bis (thiophene-2-carboxylato) zinc [Zn(tc)2], bis(thiophene-2-acetato)Zn [Zn(ta)2], (N-acetyl-L-cysteinato) Zn(II) [Zn (nac)], Zn(II)/poly(γ-glutamic acid) [Zn(γ-pga)], bis (pyrrolidine-N-dithiocarbamate) zinc(II) [Zn(pdc) 2], Zn(II) L-lactate [Zn(lac)2], Zn(II) D-(2)-quinic acid [Zn(qui)$_2$], bis(1,6-dimethyl-3-hydroxy-5-methoxy-2-pentyl-1,4-dihydropyridine-4-thionato) zinc(II) [Zn(tanm)2], β-alanyl-L-histidinato Zn(II) (AHZ) and combinations thereof.

9. The method of claim 1, wherein the antimicrobial solution comprises $Zn^{2+}$ ions.

10. The method of claim 1, wherein the tissue graft comprises a tissue selected from allograft bone, autograft bone, xenograft bone, allograft cartilage, amniotic tissue, ligament tissue, tendon tissue, porous tissue, soft tissue, and a combination thereof.

11. The method of claim 1, wherein the tissue graft comprises an allograft tissue.

12. The method of claim 11, wherein the allograft tissue comprises allograft bone.

13. The method of claim 1, wherein the tissue graft comprises amniotic tissue or cartilage.

14. The method of claim 1 wherein the antimicrobial solution is effective against microbial organisms selected from the group consisting of *Pseudomonas aeruginosa, Staphylococcus aureus, Aspergillus brasiliensis* spores, *Escherichia coli*, and *Mycobacterium tuberculosis*.

15. The method of claim 1, wherein the antimicrobial solution further comprises a pharmaceutically acceptable vehicle, excipient, diluent, or adjuvant.

16. A tissue graft prepared by the method of claim 1, wherein the tissue graft is penetrated by the antimicrobial solution and comprises a surface of the tissue graft modified by the zinc compound.

17. The tissue graft of claim 16, wherein the tissue graft comprises a tissue selected from allograft bone, autograft bone, xenograft bone, allograft cartilage, amniotic tissue, ligament tissue, tendon tissue, porous tissue, soft tissue, and a combination thereof.

18. The tissue graft of claim 16, wherein the tissue graft comprises an allograft tissue.

19. The tissue graft of claim 18, wherein the allograft tissue comprises allograft bone.

20. A kit comprising the tissue graft of claim 16.

* * * * *